United States Patent [19]
Kawae et al.

[11] Patent Number: 4,961,957
[45] Date of Patent: Oct. 9, 1990

[54] METHOD OF PRODUCING AN ELECTROCHEMICAL CELL HAVING A POROUS ELECTRODE OR ELECTRODES

[75] Inventors: Takayuki Kawae; Kazuyoshi Shibata, both of Nagoya, Japan

[73] Assignee: NGK Insulators, Ltd., Japan

[21] Appl. No.: 386,607

[22] Filed: Jul. 31, 1989

[30] Foreign Application Priority Data

Aug. 3, 1988 [JP] Japan .................................. 63-194263

[51] Int. Cl.$^5$ ........................................... G01N 27/409
[52] U.S. Cl. ..................................... 427/125; 204/424; 427/126.3; 427/245; 427/383.5
[58] Field of Search ................. 204/424; 427/229, 245, 427/126.3, 125

[56] References Cited

U.S. PATENT DOCUMENTS

| | | | |
|---|---|---|---|
| 4,209,377 | 6/1980 | Shinohara et al. | 204/424 |
| 4,283,441 | 8/1981 | Haecker et al. | 204/424 X |
| 4,610,741 | 9/1986 | Mase et al. | 204/424 X |

FOREIGN PATENT DOCUMENTS 123351 6/1987 Japan .

Primary Examiner—G. L. Kaplan
Attorney, Agent, or Firm—Arnold, White & Durkee

[57] ABSTRACT

An electrochemical cell which includes a solid electrolyte body and a plurality of electrodes formed on the solid electrolyte body, for determining the concentration of a component contained in a measurement gas. The electrodes include at least one porous electrode exposed to the measurement gas. The method includes a step of preparing an unfired electrode material for the porous electrode or electrodes, which includes an inorganic compound which produces a gas at an elevated temperature, and an electrically conductive material. The unfired electrode material is applied to the solid electrolyte body to form an unfired electrode layer or layers corresponding to the porous electrode or electrodes. The formed unfired electrode layer or layers is/are heated to a temperature higher than the above-indicated elevated temperature, to form the porous electrode or electrodes.

5 Claims, 2 Drawing Sheets

METHOD OF PRODUCING AN ELECTROCHEMICAL CELL HAVING A POROUS ELECTRODE OR ELECTRODES

BACKGROUND OF THE INVENTION

1. Field of the Invention

The present invention relates generally to a method of producing an electrochemical cell using a solid electrolyte, more particularly, to a method of producing a porous measuring electrode which is used on such an electrochemical cell for detecting or determining the concentration of a desired component contained in a subject gas, and which is exposed to the subject gas.

2. Discussion of the Prior Art

In the art of detecting the concentration of a desired component contained in a subject gas, there is known a gas sensor incorporating an electrochemical cell which has a solid electrolyte body and a plurality of electrodes formed on the solid electrolyte body. For determining the concentration of oxygen in an exhaust emission produced by an internal combustion engine of a motor vehicle as a result of combustion of an air-fuel mixture, for example, an oxygen sensor is commonly used which employs an oxygen-ion conductive zirconia ceramic as the solid electrolyte body. This oxygen sensor is operated to sense the oxygen concentration, according to the principle of an oxygen concentration cell, or by utilizing an electrochemical oxygen pumping action, or such an oxygen pumping action combined with the principle of diffusion of the measurement gas, i.e., a restricted flow of the measurement gas due to a flow resistance provided by suitable means.

In an internal combustion engine, such an oxygen sensor as described above is generally used for the purpose of accurately regulating the air/fuel (A/F) ratio of an air-fuel mixture supplied to the internal combustion engine, so that the air/fuel ratio is maintained at an optimum value. Since the oxygen concentration of the exhaust gases emitted by the engine has a known relationship with the air/fuel ratio of the air-fuel mixture, the air/fuel ratio can be determined by detecting the oxygen concentration of the exhaust emission. The output of the oxygen sensor, namely, an electromotive force induced in the electrochemical cell is indicative of the air/fuel ratio, and is fed back to a control device for regulating the amount of supply of the fuel to the engine. To this end, the characteristics of the oxygen sensor in connection with the electromotive force relative to the oxygen concentration of the exhaust emission, and the time of a response of the sensor to a change in the oxygen concentration are basically important for accurate regulation of the air/fuel ratio of the air-fuel mixture. In particular, the oxygen sensor is required to demonstrate an excellent operating response In addition to these basic characteristics, the magnitude of polarization upon application of an electric current to the electrochemical cell is also a key factor of the sensor, from the standpoint of protecting the solid electrolyte body of the cell against deterioration due to the polarization. Further, it is recognized that the sensing accuracy and operating response of the oxygen sensor can be improved by reducing a deviation of the electromotive force induced by the electrochemical cell, from the theoretical or nominal value at a varying level of the oxygen concentration of the exhaust gases.

In the electrochemical cell used for sensors such as an oxygen sensor as described above, the electrodes provided on the solid electrolyte body are usually given a porous structure for obtaining a relatively large number of triple points (points of reaction) among the solid electrolyte, a metal of the electrodes and the measurement gas. For instance, the porous electrodes are formed by co-firing unfired layers of the electrodes together with an unfired body of the solid electrolyte material. This co-firing method to obtains a porous structure of the electrodes due to on a difference between the sintering temperatures of the material of the solid electrolyte body and the material (in the form of a paste) of the electrodes. However, since the sintering temperature of the solid electrolyte material is higher than that of an electrically conductive metal such as platinum contained in the material of the electrodes, the conductive metal of the electrodes is sintered at the co-firing temperature, whereby the fired electrodes cannot be made sufficiently porous. Accordingly, the electrochemical cell having the thus formed electrodes, and the sensor using this cell do not provide satisfactory characteristics, particularly in terms of the operating response.

SUMMARY OF THE INVENTION

It is therefore an object of the present invention to provide a method of producing an electrochemical cell including an electrode or electrodes having a sufficiently porous structure. Another object of the invention is to provide a method of producing an electrochemical cell by co-firing unfired materials of a solid electrolyte body and an electrode or electrodes so that the fired electrode or electrodes is/are sufficiently porous.

The above objects may be achieved according to the principle of the present invention, which provides a method of producing an electrochemical cell. The method includes a solid electrolyte body and a plurality of electrodes formed on the solid electrolyte body, for determining the concentration of a component contained in a measurement gas, the electrodes including at least one porous electrode exposed to the measurement gas. The method comprises the steps of: preparing an unfired electrode material for the above-indicated at least one porous electrode exposed to the measurement gas, the unfired electrode material comprising an inorganic compound which produces a gas at an elevated temperature, and an electrically conductive material; applying the unfired electrode material to the solid electrolyte body, an to form an at least one unfired electrode layer corresponding to the above-indicated at least one porous electrode; and heating the formed at least one unfired electrode layer. The above-indicated at least one porous electrode is formed thereby.

In the method of the present invention for producing an electrochemical cell as described above, at least the electrode or electrodes exposed to the measurement gas is/are formed of an electrode material which comprises the inorganic compound which produces a gas at an elevated temperature, and the electrically conductive material. This electrode material is applied to a suitable position or positions on the solid electrolyte body, and is heated or baked for integral bonding to the solid electrolyte body. Upon heating the unfired electrode material to a temperature higher than the above-indicated elevated temperature, the inorganic compound of the electrode material produces a gas, which prevents the electrode material from being sintered and densified, thereby providing the fired electrode or electrodes with a sufficiently porous structure, i.e., a high degree of porosity.

The electrode having a porous structure, thus obtained by means of gasification of the inorganic compound, is effectively given a large number of triple points among the solid electrolyte material, the electrically conductive material of the electrode and the measurement gas, whereby the response characteristic of the electrochemical cell is improved. In addition, the cell-induced electromotive force changes with the concentration of the subject component of the measurement gas, according to the theoretical or nominal relationship curve. Further, the porous structure contributes to reduction in the polarization resistance of the electrode during application of an electric current to the cell, whereby the solid electrolyte body is protected against deterioration due to the polarization resistance, and the durability of the cell is accordingly increased.

The unfired electrode material may comprise a suitable ceramic material as well as the inorganic compound and electrically conductive material indicated above. Preferably, the unfired electrode material is applied to an unfired mass of the solid electrolyte body, so that the formed unfired electrode layer or layers and the unfired solid electrolyte mass are co-fired for simultaneous sintering thereof.

DETAILED DESCRIPTION OF THE INVENTION

According to the method of the present invention, the solid electrolyte body of the electrochemical cell is formed into a suitable shape known in the art, by using a solid electrolyte selected from among conventionally used materials, depending upon the component of the measurement gas whose concentration is determined, and other factors associated with the sensor which incorporates the cell. For instance, the solid electrolyte body of the electrochemical cell used for an oxygen sensor is formed of an oxygen-ion conductive solid electrolyte which includes $ZrO_2$ (zirconia) as a major component, and at least one additive such as $Y_2O_3$, $CaO$, $Yb_2O_3$ and $MgO$.

On the other hand, the electrically conductive material applied together with the inorganic material to the solid electrolyte body to form the porous electrode or electrodes at the predetermined position or positions on the solid electrolyte body may, for example, consist of platinum, or an alloy of platinum and another metal such as nickel, silver, gold, rhodium, palladium, iridium or ruthenium.

To improve the adhesion of the electrode or electrodes to the solid electrolyte body, the electrode material may further comprise a ceramic material such as a material used for the solid electrolyte body, or alumina, spinel or other ceramics, as needed. The proportion of the electrically conductive material, the ceramic material and the inorganic compound of the electrode material is suitably determined depending upon the specific combination of these three materials. It is noted, however, that the electrical conductivity of the electrode decreases with a decrease in the content of the electrically conductive material, while the degree of sintering of the conductive material increases with an increase in the content of the conductive material, with a result of increasing an adverse effect on the porous structure of the electrode eventually formed. In this respect, the electrode material comprises preferably up to 40 parts by weight of the ceramic material and 0.5–60 parts by weight of the inorganic compound, more preferably 10–20 parts by weight of the ceramic material and 5–15 parts by weight of the inorganic compound, per 100 parts by weight of the electrically conductive material.

The inorganic compound included in the electrode material according to the present invention produces a gas, while being burned out, vaporized or decomposed during heating of the electrode material at an elevated temperature generally not lower than 400° C., and preferably not lower than 800° C. Where the heating of the electrode material is effected concurrently with the firing of the unfired mass of the solid electrolyte body, it is desirable that the temperature at which the inorganic compound produces a gas be lower than the sintering temperature of the solid electrolyte material.

Most preferably, the inorganic compound consists of a compound which is heated into a composition similar to the solid electrolyte material or the ceramic material included in the electrode material, even if the heated compound is left as the composition after the gasification or vaporization at the elevated temperature indicated above. In this case, it is desirable that the residual composition may cooperate with the solid electrolyte material and the ceramic material of the electrode to form a solid solution. However, the heated inorganic compound may be left as a composition which may be removed by a suitable medium such as an acid, alkaline solution or water.

For providing the fired electrode with a porous structure which effectively increass the number of the triple points indicated above, the inorganic compound is preferably decomposed at a relatively high temperature. In this respect, the inorganic compound is preferably selected from the group consisting of: carbonates such as barium carbonate and strontium carbonate; hydroxides such as barium hydroxide and calcium hydroxide; peroxides such as barium peroxide; oxalates such as yttrium oxalate; acetates such as silicon acetate; sulfates such as zirconium sulfate; nitrates such as zirconium nitrate; carbides such as silicon carbide; nitrides such as silicon nitride; fluorides such as zirconium fluoride; oxides such as $PtO$; sulfides such as $PtS_2$; hydrides such as $BaH_2$; bromides such as $CaBr_2$; and chlorides such as $YCl_3$.

The unfired electrode material which comprises the electrically conductive material and inorganic compound as described above, and the ceramic material if necessary, is applied to the solid electrode body, by a suitable known technique such as a screen-printing or spraying method, so as to form an unfired electrode layer or layers having a suitable thickness, at the predetermined position or positions on the solid electrolyte body. Then, the formed unfired electrode layer or layers is/are heated for firing or baking, whereby a corresponding porous electrode or electrodes is/are formed on the solid electrolyte body, for exposure to the measurement gas. Where the screen-printing technique is used, a mixture paste of the electrically conductive material and inorganic compound, and the ceramic material if necessary, is prepared, and the unfired electrode layer or layers is/are formed of the prepared mixture by screen-printing on the solid electrolyte body. The formed unfired electrode layer or layers is/are then heated to a suitable elevated temperature. Where the spraying technique is used, the inorganic compound with or without the ceramic material is added to a solution containing the electrically conductive material. The thus obtained solution is sprayed over the predetermined area or areas on the solid electrolyte body, to form an unfired electrode layer or layers. The unfired layer or layers is/are fired into the corresponding porous electrode or electrodes.

The solid electrolyte body may be fired or sintered before the unfired electrode material is applied thereto. However, the unfired electrode material is preferably applied to an unfired mass or green body of the solid electrolyte which has not been sintered. In this case, the unfired electrode layer or layers is/are co-fired with the unfired solid electrolyte mass, so that the porous electrode or electrodes is/are formed while the unfired solid electrolyte is sintered.

While the process of forming the porous electrode or electrodes by using the unfired electrode material as described above is advantageously applied to at least an electrode or electrodes which is/are exposed to the measurement gas, the present process using the electrode material according to the invention is applicable to the formation of a porous electrode or electrodes which is/are not exposed to the measurement gas. It will be understood, however, that the electrode or electrodes not exposed to the measurement gas may be formed by a method conventionally practiced in the art.

Each porous electrode formed by the method described above may be covered by a suitable protective layer. This protective layer is preferably a porous layer formed of alumina or a material having similar properties as the material of the solid electrolyte body, but may be formed of any material which is conventionally used for a protective layer for protecting an electrode against corrosion, vaporization and other undesirable phenomenon. Such a protective layer may be formed such that the unfired electrode layer and the unfired protective layer formed on the unfired electrode layer are co-fired. Alternatively, the unfired protective layer is applied so as to cover the porous electrode already formed on the solid electrolyte body, and the unfired protective layer is fired. Further, the fired protective layer is first prepared, and the unfired solid electrolyte body and the unfired electrode layer are formed on the protective layer and are then co-fired. However, it is desirable to prepare an unfired laminar structure consisting of the unfired solid electrolyte body, unfired electrode layer and unfired protective layer, and heat the unfired laminar structure for simultaneous firing the three members. In this case, the material of the protective layer preferably has substantially the same shrinkage factor as the solid electrolyte material.

BRIEF DESCRIPTION OF THE DRAWINGS

The above and other objects, features and advantages of the present invention will become more apparent by reading the following description of examples of an electrochemical cell produced according to the invention, when considered in connection with the accompanying drawings, in which.

DETAILED DESCRIPTION OF THE PREFERRED EMBODIMENTS

Figure 1:
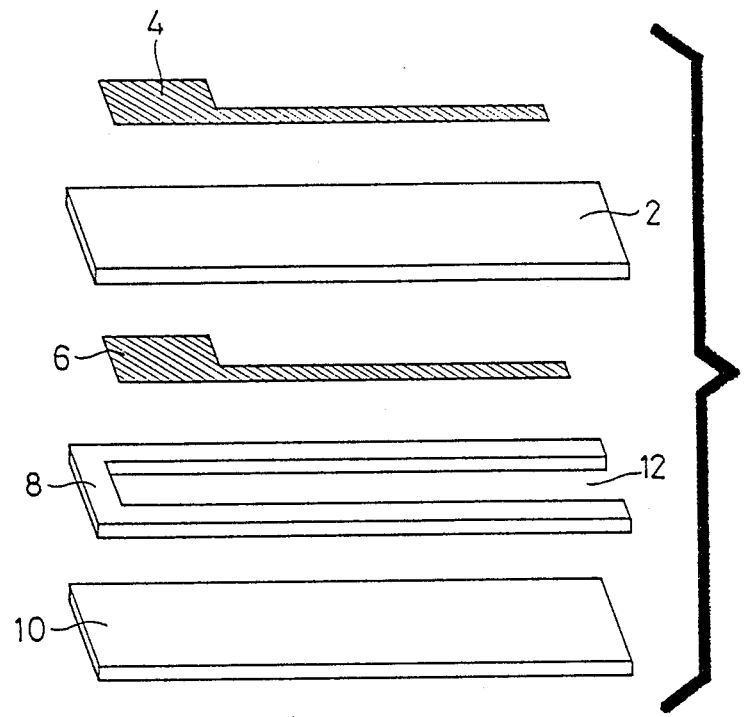
FIG. 1 is an exploded perspective view of one form of an electrochemical cell to which the present invention is applicable.

Various mixtures of platinum (Pt), zirconia ($ZrO_2$) and inorganic compound as indicated in Table 1 were prepared. To each of these mixtures were added 5 parts by weight of ethyl cellulose and 100 parts by weight of terpinol. The obtained mixtures were uniformly kneaded into electrode pastes A through M, as indicated in Table 1. By using each of these electrode pastes A–M, unfired electrode layers 4 and 6 were formed by screen-printing on opposite major surfaces of a green sheet 2 of zirconia ($ZrO_2$) as a solid electrolyte material. On the zirconia green sheet 2 with the unfired electrode layers 4, 6 formed, there were formed an unfired spacer member 8 of $ZrO_2$ and an unfired covering member 10 of $ZrO_2$ such that the unfired electrode layer 6 was exposed to an air passage 12 defined by an elongate slot which was formed through the spacer member 8 and closed by the zirconia green sheet 2 and unfired covering member 10. Thus, an unfired laminar structure 2, 4, 6, 8, 10 was prepared. This unfired laminar structure was fired at 1450° C. As a result, the unfired

TABLE 1

| Electrode Paste | Pt (parts) | $ZrO_2$ (parts) | Inorganic Compound Composition | (parts) | (°C.)* |
|---|---|---|---|---|---|
| A | 100 | 19 | — | — | — |
| B | " | 23 | $BaCO_3$ | 0.6 | 1350 |
| C | " | 14 | " | 6.0 | " |
| D | " | " | " | 14.0 | " |
| E | " | 0 | $Zr(OH)_4$ | 30.0° | 440 |
| F | " | 14 | " | 7.0 | " |
| G | " | " | $Y_2(C_2O_4)_3 \cdot 9H_2O$ | " | 410 |
| H | " | " | $Ba(OH)_2 \cdot 8H_2O$ | " | 890 |
| I | " | " | $Zr(SO_4)_2 \cdot 4H_2O$ | " | 380 |
| J | " | " | ZrC | " | 1350 |
| K | " | " | $Si(CH_3COO)_4$ | " | 180 |
| L | " | " | $SrCO_3$ | " | 1155 |
| M | " | " | PtO | " | 550 |

Note:
(1) The contents of Pt, $ZrO_2$ and inorganic compound are expressed in parts by weight.
(2) (°C.)* indicates the decomposition point of the inorganic compound electrode layers 4, 6 were fired and baked concurrently with the sintering of the zirconia green sheet 2 and the unfired spacer and covering members 8, 10. In this manner, there were prepared various electrochemical cells corresponding to the pastes A–M. Each of the cells has a first porous electrode (4) formed on an outer major surface of a $ZrO_2$ solid electrolyte body (2), for exposure to an external measurement gas, and a second porous electrode (6) formed on an inner major surface of the solid electrolyte body (4), for exposure to a reference gas in the form of an ambient air introduced into the air passage 12.

The prepared electrochemical cells, which will be referred to as cells A–M, corresponding to the electrode pastes A–M used, were tested as an oxygen sensing cell, for evaluating the operating response, a variation in the electromotive force with a changing oxygen concentration of a subject gas (measurement gas), and a DC impedance when the cells were operated to effect an oxygen pumping action. The test was conducted in the following manner.

For evaluating the operating response, each electrochemical cell A–M was exposed to the subject gas in the form of a combustion gas emitted by a propane gas burner, to detect the oxygen concentration of the subject gas, while the oxygen concentration of the gas was changed by changing the air/fuel ratio of an air-fuel mixture supplied to the gas burner. More specifically, the air-fuel mixture was changed from a fuel-lean air-fuel mixture to a fuel-rich air-fuel mixture, or vice versa. The fuel-lean air-fuel mixture has an air/fuel ratio lower than the stoichiometric point of 14.6 (equivalent to the excess air ratio λ of 1), while the fuel-rich air-fuel mixture has an air/fuel ratio higher than the stoichiometric point.

Figure 2A:
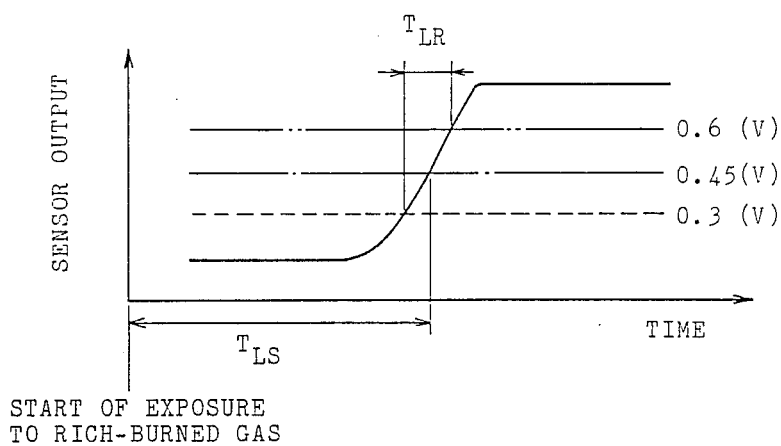
FIGS. 2(a) and 2(b) are graphs for explaining the response time of various examples of the electrochemical cell produced according to the invention.

Initially, each electrochemical cell was exposed to a lean-burned gas produced as a result of combustion of the fuel-lean air-fuel mixture supplied to the gas burner. The air/fuel ratio of the air-fuel mixture was gradually changed so that the cell was exposed to a rich-burned gas produced as a result of combustion of the fuel-rich air-fuel mixture. The point of time at which the exposure of the cell to the rich-burned gas was started is indicated in FIG. 2(a). After this point of time, an electromotive force induced by the cell increased. A time $T_{LR}$ indicated in FIG. 2(a) represents a duration between the points of time at which the electromotive force reached 0.3 V and 0.6 V respectively. An increase in the electromotive force beyond a threshold level of 0.45 V (corresponding to the stoichiometric point of the air/fuel ratio) indicates a change of the combustion gas from the lean-burned gas to the rich-burned gas. A time $T_{LS}$ also indicated in FIG. 2(a) represents a time interval between the moment at which the exposure of the cell to the rich-burned gas was started, and the moment at which the electromotive force of the cell reached the threshold level of 0.45 V.

Figure 2B:
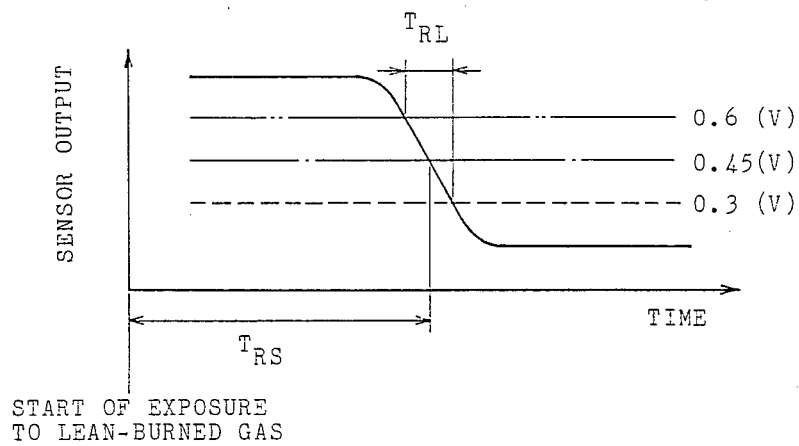

The graph of FIG. 2(b) shows the variation of the electromotive force of the cell when the cell was first exposed to the rich-burned gas, and then exposed to the lean-burned gas as indicated at the left end of a time interval $T_{RS}$. This time interval $T_{RS}$ terminates at the moment when the electromotive force has been lowered down to the threshold level of 0.45 V. A time $T_{RL}$ represents a duration between the points of time at which the electromotive force has been lowered to 0.6 V and 0.3 V, respectively. It will be understood that the time intervals $T_{LS}$ and $T_{RS}$ substantially represent a response time of the cell, i.e., a time required for the cell to detect a change of the combustion gas from the lean-burned gas to the rich-burned gas, or vice versa (namely, a change of the air-fuel mixture from the fuel-lean one to the fuel-rich one, or vice versa).

The time intervals $T_{LS}$ and $T_{RS}$, and the times $T_{LR}$ and $T_{RL}$ of all the cells A–M were measured. The measurements are indicated in Table 2.

For detecting a variation in the electromotive force, the cells were placed in a prepared specimen gas (containing $N_2$, $CO_2$, CO, $H_2$, NO and $C_3H_8$) at 350° C. and operated as an oxygen sensor. During the operation of each cell air was added into the specimen gas to detect a consequent decrease in the electromotive force inducted by the cell. A value λs of the excess air ratio λ of the specimen gas containing the air was measured at the time when the electromotive force of 0.45 V was detected. The measurements are indicated in Table 2.

The DC impedance of the cells was measured by applying a DC current of 300 mV between the first and second electrodes (4, 6) to effect an oxygen pumping action. The measurements of the DC impedance are also indicated in Table 2.

TABLE 2

| Cell | Evaluation of Cell Response | | | | | Excess Air Ratio (λs) | DC Impedance (kΩ) |
|---|---|---|---|---|---|---|---|
| | $T_{RL}$ (ms) | $T_{LR}$ (ms) | $T_{RS}$ (ms) | $T_{LS}$ (ms) | $T_{RS} + T_{LS}$ (ms) | | |
| A | 22 | 16 | 221 | 156 | 377 | 1.019 | 2.360 |
| B | 17 | 9 | 164 | 117 | 281 | 1.010 | 1.950 |
| C | 13 | 6 | 148 | 108 | 256 | 1.007 | 1.730 |
| D | 12 | 7 | 138 | 109 | 247 | 1.007 | 1.810 |
| E | 13 | 7 | 136 | 107 | 243 | 1.008 | 1.830 |
| F | 10 | 4 | 122 | 106 | 228 | 1.007 | 1.750 |
| G | 9 | 4 | 122 | 101 | 223 | 1.006 | 1.740 |
| H | 9 | 4 | 117 | 100 | 217 | 1.007 | 1.770 |
| I | 10 | 5 | 120 | 116 | 236 | 1.009 | 1.920 |
| J | 12 | 6 | 133 | 109 | 242 | 1.008 | 1.960 |
| K | 18 | 8 | 160 | 123 | 283 | 1.010 | 1.930 |
| L | 11 | 5 | 131 | 105 | 236 | 1.009 | 1.780 |
| M | 15 | 8 | 159 | 115 | 274 | 1.011 | 1.860 |

It will be understood from Table 2 that the time intervals $T_{RL}$, $T_{LR}$, $T_{RS}$, $T_{LS}$ of the electrochemical cells B through M having the porous electrodes (4, 6) according to the present invention are considerably shorter than those of the electrochemical cell A which has known electrodes, which are formed of a composition not containing an inorganic compound as used in the present invention. Thus, the cells according to the invention exhibited improved operating response.

Further, the cells B–M having the porous electrodes formed according to the present invention exhibited a relationship between the electromotive force and the oxygen concentration or excess air ratio of the specimen gas, which is closer to the nominal relationship. More specifically, the excess air ratios measured when the electromotive force of the cells B–M was 0.45 V are closer to 1.0 (corresponding to the stoichiometric air/fuel ratio of 14.6), than the excess air ratio measured when the electromotive force of the cell A was 0.45 V. This means that the cells B–M according to the invention are capable of more accurate detection of the air-fuel mixture which has the stoichiometric air/fuel ratio (equivalent to the excess air ratio of 1).

While the concept of the present invention has been clarified by the foregoing detailed description together with the illustration of examples of the electrochemical cell produced according to the presently preferred forms of the invention, it is to be understood that the invention is not bound by the detailed description and is not limited to the details of the illustrated examples, but may be embodied with various changes, modifications and improvements, which may occur to those skilled in the art, without departing from the spirit and scope of the invention defined in the following claims.

What is claimed is:

1. A method of producing an electrochemical cell, said electrochemical cell comprising a solid electrolyte body co-fired with a plurality of electrodes formed on said solid electrolyte body and being used for determining the concentration of a component in the measurement gas, said plurality of electrodes including at least one porous electrode exposed to a measurement gas, said method comprising the steps of:

preparing an unfired electrode material which comprises an inorganic compound that produces a gas at an elevated temperature, a ceramic material consisting essentially of zirconia and an electrically conductive material;

applying said unfired electrode material on an unfired solid electrolyte body to form an electrode layer thereon; and heating said electrode layer and said unfired solid electrolyte body to a temperature above said elevated temperature to co-fire said electrode layer with said unfired solid electrolyte body, thereby forming said porous electrode on said solid electrolyte body.

2. A method according to claim 1, wherein said inorganic compound is selected from the group consisting of carbonates, hydroxides, peroxides, oxalates, acetates, sulfates, nitrides, carbides, oxides, sulfides, hydrides, bromides and chlorides.

3. A method according to claim 1, wherein said electrically conductive material is selected from the group consisting of platinum, nickel, silver, gold, rhodium, palladium, iridium and ruthenium.

4. A method according to claim 1, wherein said inorganic compound produces a gas during decomposition thereof.

5. A method according to claim 1, wherein said unfired electrode material comprises 0.5–60 parts by weight of said inorganic compound and up to 40 parts by weight of said ceramic material, per 100 parts by weight of said electrically conductive material.

* * * * *